United States Patent [19]

Shimbashi

[11] Patent Number: 4,619,611
[45] Date of Patent: Oct. 28, 1986

[54] DENTAL ARTICULATOR

[76] Inventor: Henry Shimbashi, Box 2352, Towers Building, Drayton Valley, Alberta, Canada, T0E 0M0

[21] Appl. No.: 737,655

[22] Filed: May 24, 1985

[30] Foreign Application Priority Data

Jul. 16, 1984 [CA] Canada ................................ 458930

[51] Int. Cl.$^4$ .............................................. A61C 11/00
[52] U.S. Cl. ........................................ 433/55; 433/54; 433/56; 433/65
[58] Field of Search ....................... 433/55, 54, 56, 57, 433/58, 59, 60, 61, 62, 63, 64, 65, 66, 67, 72, 73

[56] References Cited

U.S. PATENT DOCUMENTS

| 198,853 | 1/1878 | Oehlecker | 433/57 |
| 1,102,741 | 7/1914 | Hardie | 433/65 |
| 1,687,864 | 10/1928 | Hill | 433/55 |
| 2,608,762 | 9/1952 | Fox | 433/57 |
| 2,621,407 | 12/1952 | Schlesinger | 433/60 |
| 2,670,538 | 3/1954 | Thompson | 433/55 |
| 3,097,431 | 7/1963 | Harris | 433/54 |
| 3,429,045 | 2/1969 | Anderson et al. | 433/54 |
| 4,182,039 | 1/1980 | Preti | 433/54 |
| 4,265,619 | 5/1981 | Lucki et al. | 433/54 |
| 4,480,995 | 11/1984 | Tate | 433/65 |

Primary Examiner—John J. Wilson
Attorney, Agent, or Firm—Cushman, Darby & Cushman

[57] ABSTRACT

A rigid, non-yielding precision dental articulator instrument for preserving and making available the occlusion plane required to build accurate incuspation of teeth. The device provides initial mounting of maxillary models using a facebow. A 20 degree sliding mounting plate is also provided for aiding in the setting of the Occlusal Plane.

3 Claims, 20 Drawing Figures

CONDYLAR MOVEMENTS [MEASURED BY THE S.S. -19 MYOCHECK]

RIGHT HORIZONTAL       [top view]       LEFT HORIZONTAL X to O = \_\_\_\_                        X to O = \_\_\_\_

----X = ORIGINAL CENTRIC OCCLUSION
____O = NEW MYOCENTRIC OCCLUSION

RIGHT VERTICAL       [side view]       LEFT VERTICAL X to O = \_\_\_\_                        X to O = \_\_\_\_

ANTERIOR VERTICAL CHANGE = \_\_\_\_\_\_\_\_

TOTAL DYSFUNCTION FACTOR = \_\_\_\_\_\_\_\_

DENTAL ARTICULATOR

FIELD OF THE INVENTION

This invention relates to dental articulators and in particular to an articulator having a rigid, non-yielding structure for providing the occlusion plane required to build accurate intercuspation of teeth.

BACKGROUND OF THE INVENTION

The articulator of the present invention was developed as a result from studies in the field of Gnathology and, to be more specific, studies of a syndrome known as Neuromuscular Dysfunction, a syndrome which is medically and dentally related. Abnormal mandibular positioning can be translated into stress related symptoms of various kinds such as headaches, muscle spasms in the head and neck etc. I have found that a substantial amount of stress can be reduced by proper mandibular positioning. The lower jaw or mandible has a relationship to the upper jaw or maxilla. When this relationship is altered, the muscles of mastication may go into spasm. This causes those muscles that have the same nerve innervation to also go into spasm with the result that stresses may radiate throughout the head, neck and may even involve the back.

The lower jaw may be overclosed (too close to the upper jaw) and/or distally displaced, (too far back in the joint or socket). Additionally, the lower jaw may deviate to one side due to interfering tooth cusps or points on the chewing surfaces of teeth that do not meet properly with the opposing teeth. The cause of jaw misclosure is usually multifaceted, i.e., loss of teeth or poor alignment thereof; natural wear of teeth; grinding or clenching of the teeth; poor tongue position, muscle unbalance between the tongue and facial muscles; chronic mouthbreathing, etc.

The diagnosis, treatment and cure of Neuromuscular Dysfunction problems has been rapidly advanced in the last few years with the introduction of certain electronic instrumentation into the dental office. Specifically, this instrumentation was that developed by Dr. Bernard Jankelson and John Radke and consists of the following:

(a) The Bio-Tens TM, an instrument for accomplishing transcutaneous electrical neural stimulation through the fifth and seventh nerves to relax the mandibular muscles and precisely control their contractions during clinical procedures. This instrument is described in U.S. Pat. No. 3,593,422.

(b) The mandibular kinesiograph (MKG), U.S. Pat. No. 3,822,694, an electronically accurate tracking instrument which easily and quickly provides the kind of factual information needed to determine the most functional individual occlusal position.

(c) An Electromyograph, an instrument used to determine the degree of relaxation of a particular muscle or muscle group at rest. It also provides a precise measurement of the relative levels of contraction of several muscles during a functional act.

The articulator of the present invention provides the mechanical portion of the translation of measurement from patient to the laboratory and back to the patient.

SUMMARY OF THE INVENTION

If it is determined that an improper relationship exists between the upper and lower jaw the muscles of mastication are relaxed and the lower jaw is closed on a trajectory that is not strained. In other words, the mouth closes where the muscles are most comfortable. The recordings from the Mandibular TM kinesiograph enable a dentist to diagnose an overclosure or malocclusion and/or an abnormal displacement of the lower jaw. The articulator of the present invention is used in developing a bite plane or splint to open the bite of the patient if there is an overclosure.

In the study of 500 neuromuscular dysfunction cases, I have found that the vertical measurement in Neuromuscular centric TM from the normal crest of the gingival of the upper central incisor to the crest of the gingival of the lower central incisor is approximately 19 mm. This is a basic guideline in bringing the lower mandible into occlusion. I have found that if the measurement is 2 mm or more under the 19 mm guideline, a case of "overcloser" exists. Conversely if the measurement is 2 mm or more above the 19 mm guideline, then an "overopened" situation exists. Another 19 mm measurement is in the final reconstruction of the maxillary-mandibular case. By working from the lower jaw, I have found that from the lower anterior vestibule to the level of the lower central incisal edge is approximately 19 mm. However, these measurements could vary approximately 1 mm either way.

The final measurement is done through the BIO-TENS TM and the mandibular kinesiograph which actually places the mandible in the proper vertical-anteroposterior and lateral position, the 19 mm measurement being a minor guideline in doing an initial set-up.

The articulator of the present invention is sufficiently solid that it retains vertical and horizontal positions. With every change in vertical dimension of the mandible there is an accompanying change in horizontal and lateral positions. The direction and the amount varies and is unpredictable from person to person. For every millimeter the mouth closes vertically, the mandible simultaneously moves anteriorly one-half a millimeter on the average and to a lesser extent there is a position change laterally.

Once the occlusal position has been registered in the patients mouth and transferred to the articulator, any change in the vertical dimension of the articulator will lose the accuracy of the horizontal position that is registered in the mouth. However, once a case is mounted on the articulator of the present invention, the vertical will not change.

The articulator of the invention does not require any condylar elements as border movements do not occur during function and research has shown that the precise construction of occlusion to the relaxed neuromuscular "home plate" position is the primary criterion for successful prosthodontics.

The articulator of the invention can also be advantageously used in the manufacture of orthodontal appliances, fixed and removable prosthodomtics and correcting pieces for the mouth.

According to a broad aspect, the invention relates to a dental articulator having a rigid, non-yielding structure for providing the occlusion plane required to build accurate intercuspation of teeth, said articulator comprising a lower mounting plate adapted to support a mandibular model, an upper mounting plate adapted to support a maxillary model, and a centre or spine post spacing said upper and lower mounting plates from one another; means rigidly securing the lower mounting plate to the lower end of said spine post; hinge means pivotally mounting the upper mounting plate to the top of the spine post and means for locking the upper mounting plate to the spine post in rigid, parallel location with respect to the lower mounting plate.

BRIEF DESCRIPTION OF THE DRAWINGS

The invention is illustrated in the accompanying drawings in which.

GENERAL DESCRIPTION

The articulator of the present invention has a "double stop" system which completely eliminates vertical height collapse. When the posterior remount pin is removed, the solid posterior stop acts independently to ensure precise maintenance of vertical height while allowing unlimited access.

The neuromuscular centric TM terminal occlusion produced on the articulator results in minimal deflective contacts that trigger bruxing or clenching. Stable occlusion is therefore provided.

The laboratory procedures pinpoint the terminal occlusion that occurs during mastication and swallowing.

The final adjustments to eliminate any interferences during access into that occlusion are effectively, realistically and quickly done by final adjustment in the mouth.

DETAILED DESCRIPTION

Figure 1:
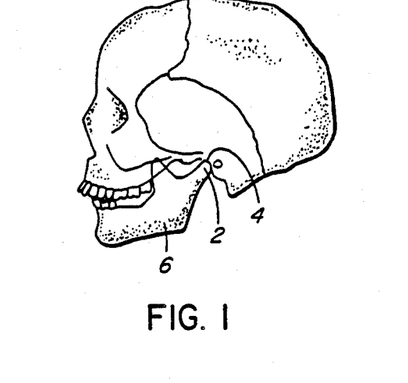
FIGS. 1-4 inclusive are skeletal views showing translation of the mandible in various vertical positions.

FIGS. 1 through 4 are skeletal views of the mandible in various vertical positions. FIG. 1 shows a partial loss where the distal drive of the condyle 2 is into the back wall of the glenoid fossa 4.

Figure 2:
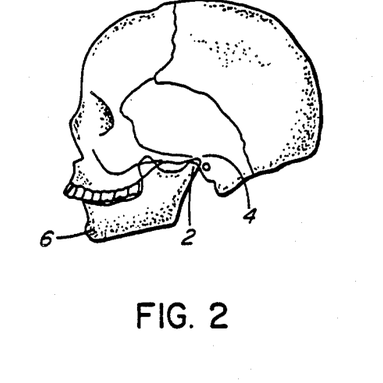

In FIG. 2, a total loss of vertical position is shown where the condyle 2 has been driven into the back wall 4 of the glenoid fossa and which can cause erosion of the condyle head.

Figure 3:
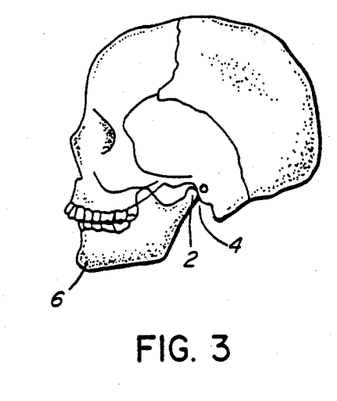

FIG. 3 shows a position where the condyle 2 is too far back and up into the glenoid fossa 4.

Figure 4:
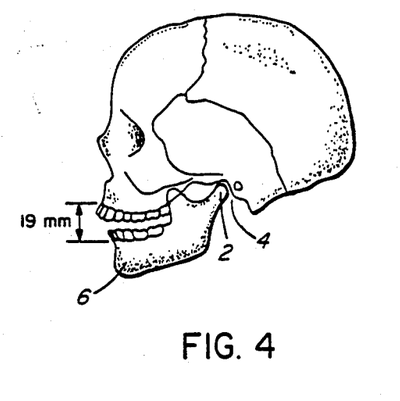

FIG. 4 shows the mandible 6 in a relaxed neuromusclar or neuromuscular centric TM position where the vertical measurement from the normal crest of the gingival of the upper central incisor to the crest of the gingival of the lower central incisor is approximately 19 mm. All orthotics, repositioners and sports splints should be made to this terminal position.

In the diagnosis of skeletal relation of the mandible to the skull a registration is taken by the dentist and transferred to the articulator. The mounting thus becomes a diagnostic tool. When the dentist makes a clinical judgement, a splint with accurate occlusion can be made on that mounting.

If the procedure is one of full mouth reconstruction, once all the teeth have been prepared a acrylic registration of the patient is taken to the neuromuscular centric position (FIG. 4) with a BIO-TENS TM and the registration is mounted on the articulator. The lab technician can now follow the neuromuscular technique and construct the occlusion to the neuromuscular position.

With an edentulous patient, an acrylic registration is taken to the neuromuscular centric position of FIG. 4 using a BIO-TENS TM. The cases are then mounted on the articulator and a 20° mounting plate then indicates to the technician where to set the teeth.

Clinical and lab procedures for complete mouth reconstruction, complete dentures and splint construction to the neuromuscular position are simple and uncomplicated using the articulator of the invention.

In order to relax the muscles of mastication, a gentle pulsating stimula is applied to the patient's skin for approximately one hour using the above mentioned BIO-TENS TM. The muscles become relaxed and their trajectory can be traced on the mandibular kinesiograph. This enables the dentist to diagnose the incorrect or abnormal relationship between the mandible to the maxillary process.

Figure 5:
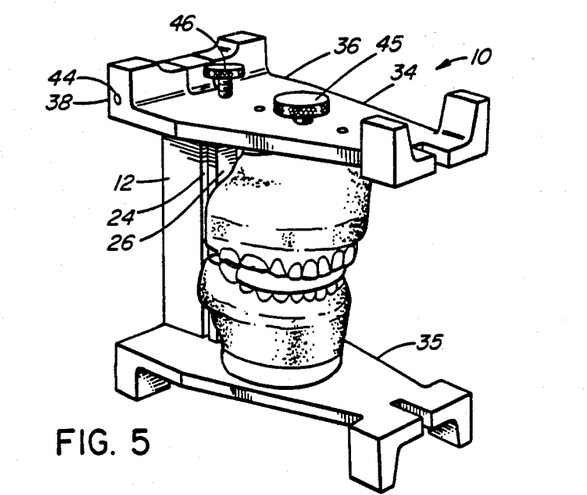
FIG. 5 is a perspective view of the articulator mounting maxillary and mandibular models.
Figure 6:
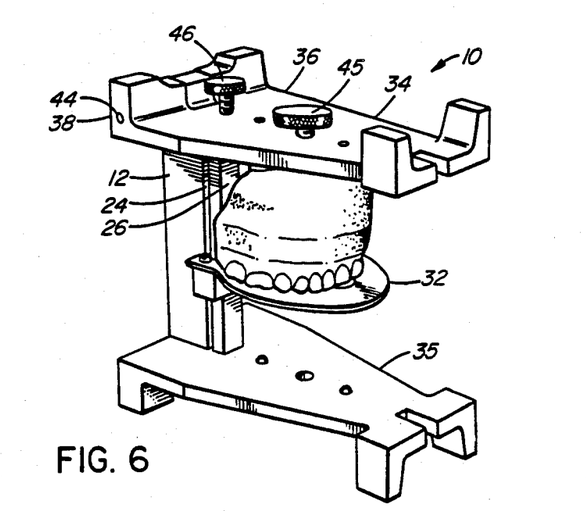
FIG. 6 is a perspective view of the articulator with the 20° mounting plate in place.
Figure 7:
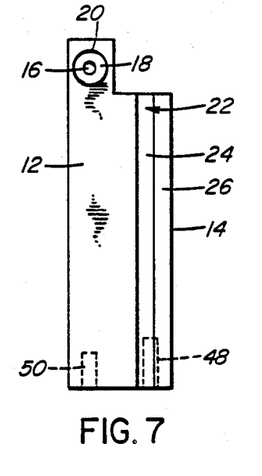
FIGS. 7 and 8 are elevation and end views respectively of the spine post.
Figure 8:
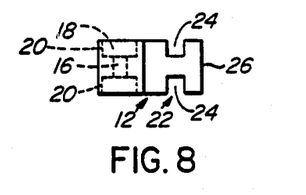
Figure 9:
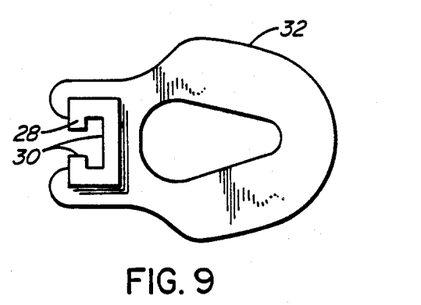
FIG. 9 is a plan view of the 20° mounting plate and adaptor.

FIGS. 5 and 6 show the articulator 10 in assembled condition and FIGS. 7 through 13 show the structural details thereof. Referring to FIGS. 7 and 8, the spine post 12 is preferably formed of a rigid light metal such as aluminum and has an elongated straight body 14 with a bore 16 through the upper end thereof, a plastic bushing 18 being located in a countersunk portion 20 of the upper end. A guide rail 22 is provided along one side of the post 12 and comprises parallel channels 24 of rectangular configuration which, together with the adjacent terminal side edge 26 of the post 12, combine to form the guide 22 of "T" shape in cross section as seen in FIG. 8. This cross section provides a plurality of guide surfaces for the reception thereon of the adaptor 28, FIG. 9, which has complimentary surfaces 30 to those of the guide rail 22 and which carries the 20° mounting plate 32.

Figure 10:
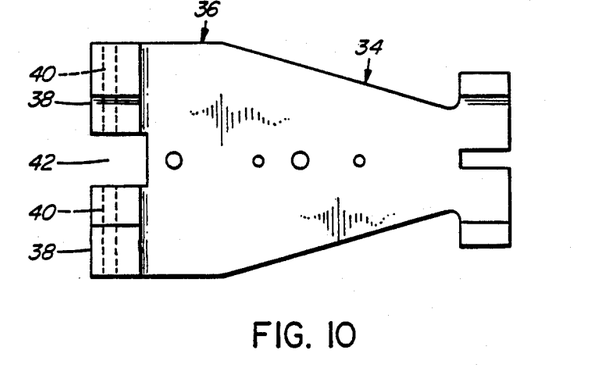
FIGS. 10 and 11 are plan and elevation views of the upper mounting plate.
Figure 11:
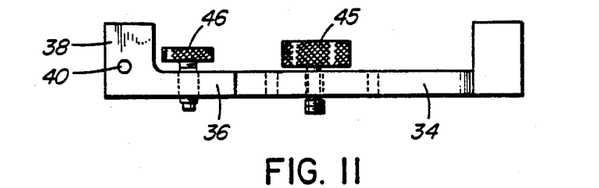
Figures 16, 17:
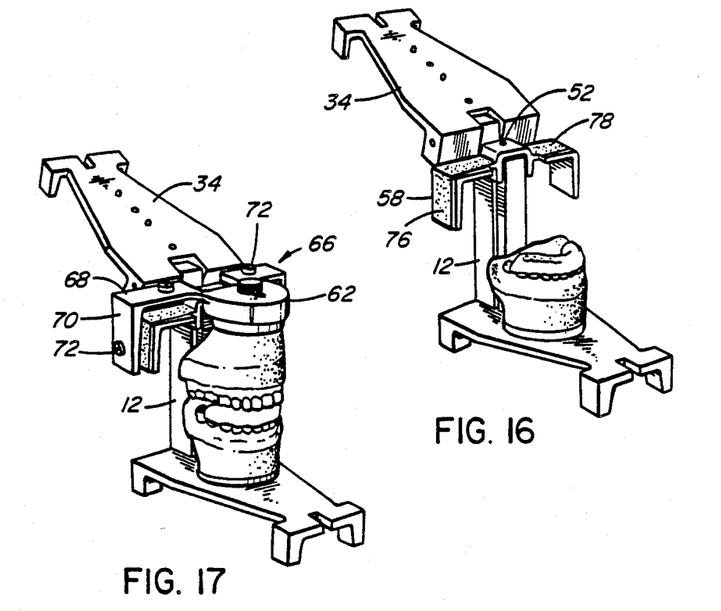
FIGS. 16, 17 and 18 are perspective views of the articulator showing various stages in obtaining Neuromuscular centric TM and centric occlusion pin points.

The upper mounting plate 34 of the articulator 10 is illustrated in FIGS. 10 and 11. The lower mounting plate or base 35, FIG. 5, is of the same construction. Plate 34 is formed of rigid aluminum of substantial thickness and includes a planar portion 36 and hinge shoulders 38 which are align bored at 40. A rectangular spacing 42 between the shoulders is provided so that the upper end of the spine post 12 is received therein, and a steel hinge pin 44, FIG. 6, pivotally interconnects plate 36 and post 12 by aligning and being located in bore 40 of the plate and bore 16 of the post. As seen in FIG. 16, the upper mounting plate 36 can be pivoted back so that it clears the upper end of the post 12. The posterior remount screw 46 is located so as to increase or decrease the vertical location of a maxillary model to or from the 19 mm guide point.

The lower mounting plate 35 is secured to the lower end of the spine post by steel locating pins 48 and 50 which enter bores provided in the lower end of the post 12, FIG. 7.

Figure 12:
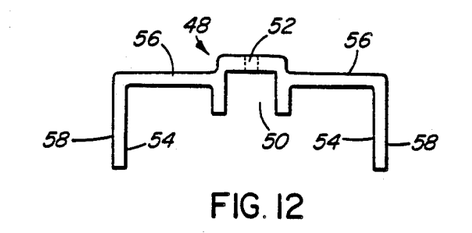
FIG. 12 is an elevation view of the inner condylar TM Kinesiograph (C.K.G.) mounting plate.

FIG. 12 shows the C.K.G. ™ inner mounting plate 48 which comprises a central channel 50 which snugly fits over the top of the spine post 12 (FIG. 16) and having an aperture 52 for receiving a locating pin. Plate 48 has a pair of L-shaped wings 54 extending outwardly and downwardly from the channel 50 to provide horizontal and vertical marking surfaces 56 and 58 respectively, FIGS. 14–16.

Figure 13:
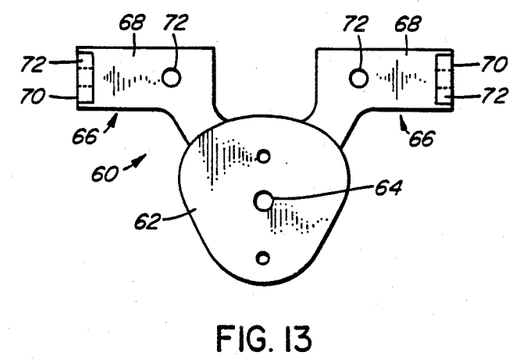
FIG. 13 is a plan view of the outer C.K.G. mounting plate.
Figure 18:
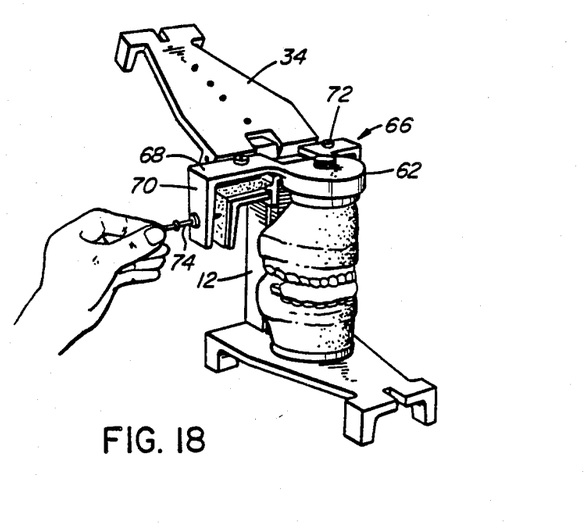

The C.K.G. ™ outer mounting plate 60 is shown in FIG. 13 and, like other elements of the articulator, it is formed of aluminum of substantial thickness and strength. A central, planar portion 62 is bored and threaded at 64 to receive a mounting screw (not shown) for attaching a mounting stone and maxillary model thereto as shown in FIG. 17. Like the inner mounting plate 48, plate 60 has a pair of L-shaped wings 66 which provide horizontal and vertical surfaces 68,70 respectively corresponding to like surfaces on the inner mounting plate 48. The surfaces 68 and 70 are provided with plastic bushings 72 for the reception of steel marking pins 74, FIG. 18.

Figure 14:
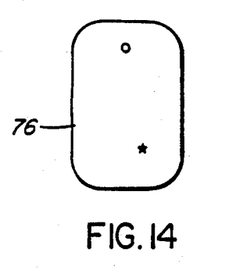
FIGS. 14 and 15 illustrate sample Neuromuscular centric TM and centric occlusion markings.
Figure 15:
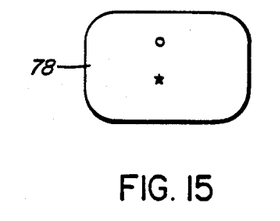

Referring to FIGS. 14 and 15 white tape or screens 76, 78 are applied to the vertical and horizontal surfaces of the inner mounting plate as shown in FIG. 16. As explained hereafter, these screens are used to indicate to the dentist the differences between the centric occlusion point and the neuromuscular centric ™ point in both horizontal and vertical planes in the condylar-glenoid fossa area.

METHOD OF OPERATION

Initially a transcranial X-ray is taken of the patient and a BIO-TENS ™ is used to bring the patient's jaw into its relaxed neuromuscular position.

Upper and lower impressions are taken and upper and lower models are made.

A Denar slideomatic facebow transfer is then used on the articulator to establish the relationship of the maxillary dentition to the horizontal reference plane so that the maxillary case can be mounted on the articulator in the correct anatomical position. The slidematic facebow provides a fast, easy and extremely accurate means of transferring the proper anatomical relationship to the articulator.

The upper model is mounted on the upper mounting plate 34 using Snow White stone and the mounting screw 45.

The dentist hand-occludes the lower to the upper and mounts the lower model to the lower plate of the articulator, measuring the vertical with calipers.

If there is an overclosure of 3 or more millimeters the articulator is opened with remount pin to 17 mm, the measurement of the normal crest of the gingiva of the upper central to the normal crest of the gingiva of the lower central.

A wafer is made using acrylic, a rolled acrylic wafer being placed on the lower teeth thereby taking up the empty space between the upper and lower models.

The magnet of the M.K.G. ™ is placed on the patient and readings are taken with the M.K.G. ™.

Models on articulator are reviewed and a bite is taken.

The lower model is removed from the white stone and spaces between teeth and under cuts are filled with blocking compound. The splint is pulled and cut out. The lower model is then re-mounted using the arcylic bite, the dentist builds the splint and checks the bite with articulating paper.

As shown in FIGS. 14–18 the inner myocheck mounting plate 48 is mounted atop the spine post 12 and tape screens 76, 78 are adhesively applied to the wing surfaces 56,58. With the teeth of the models in occlusion, the marking pins are used (FIG. 18) to mark centric occlusion points on the screens 76, 78 of the inner plate 48. Subsequently the acrylic bite block is mounted between the models and Neuromuscular centric ™ points are marked on the screens 76, 78 of the inner mounting plate.

Figure 15A:
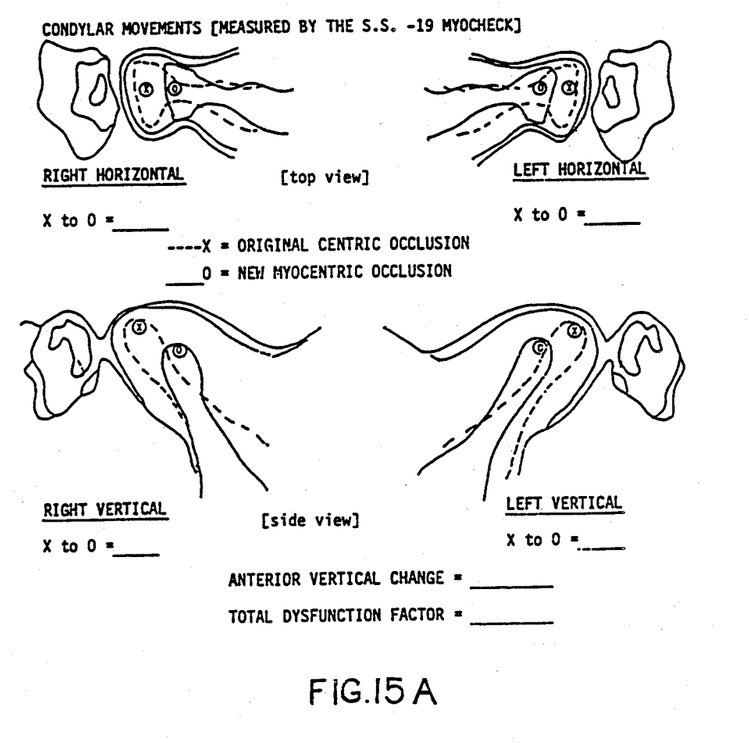
FIG. 15A illustrates movement of condyle in glenoid fossa from centric occlusion to Neuromuscular centric TM.

The distance between the markings indicating to the dentist the increase in the extra capsular space from centric occlusion to Neuromuscular centric ™, condyle to top wall, on the vertical screen and the increase in the extra capsular space from centric occlusion to Neuromuscular centric ™, condyle to back wall, on the horizontal screen as shown in FIG. 15A.

Figure 19:
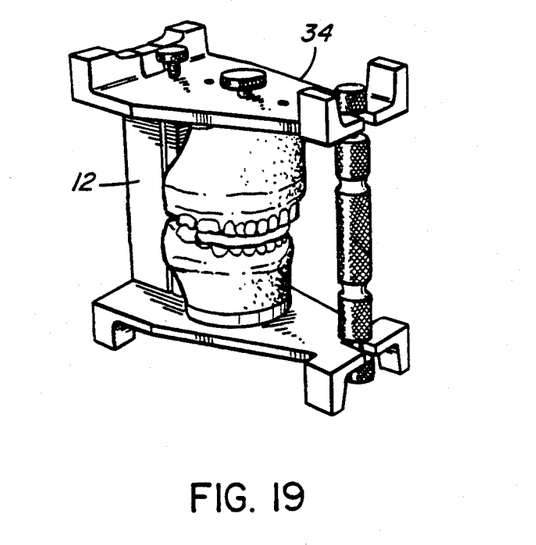
FIG. 19 shows the articulator with the myocentric post in place, the post being used in preventing any increase in the vertical during setting of mounting stone or in the fabrication of appliances on the articulator.

FIG. 19 illustrates the articulator with the Neuromuscular centric ™ post P in place, the post P being used in preventing any increase in the vertical during setting of a mounting stone or in the fabrication of appliances on the articulator.

While the invention has been described in connection with a specific embodiment thereof and in a specific use, various modifications thereof will occur to those skilled in the art without departing from the spirit and scope of the invention as set forth in the appended claims.

The terms and expressions which have been employed in this specification are used as terms of description and not of limitation, and there is no intention in the use of such terms and expressions to exclude any equivalents of the features shown and described or portions thereof, but it is recognized that various modifications are possible within the scope of the invention claimed.

The embodiments of the invention in which an exclusive property or privilege is claimed are defined as follows:

1. A dental articulator having a rigid, nonyielding structure for providing the occlusion plane required to build accurate intercuspation of teeth, said articulator comprising a lower mounting plate adapted to support a mandibular model, an upper mounting plate adapted to support a maxillary model, and a centre or spine post spacing said upper and lower mounting plates from one another; means rigidly securing the lower mounting plate to the lower end of said spine post; hinge means pivotally mounting the upper mounting plate to the top of the spine post and means for locking the upper mounting plate to the spine post in rigid, parallel location with respect to the lower mounting plate; an inner mounting plate and an outer mounting plate adapted to support said maxillary model; means on said inner mounting plate for detachable securement to said spine post and means associated with said inner mounting plate to provide first horizontal and vertical marking surfaces respectively; said outer mounting plate comprising a central planar portion for attachment thereto of a mounting stone and maxillary model and means providing second horizontal and vertical surfaces which, when said outer mounting plate is positioned on said articulator, are spaced from and correspond to said first horizontal and vertical marking surfaces of said inner mounting plate, and apertures in the vertical and horizontal surfaces of the outer mounting plate for the reception of marking means for applying marks to the surfaces of the inner mounting plate.

2. An articulator according to claim 1 including a guide rail on said spine post and an adaptor for closely and slidably engaging said guide rail; and a 20° mounting plate secured to said adaptor.

3. A dental articulator according to claim 1 wherein said means on said inner mounting plate comprises a central channel for detachable securement to the top of said spine post; and wherein the means for providing said first marking surfaces comprises a pair of L-shaped wings extending outwardly and downwardly from said central channel; said means on the outer mounting plate providing said second surfaces comprising a second pair of L-shaped wing portions extending outwardly and downwardly from said central planar portion.

* * * * *